United States Patent [19]

Hermann et al.

[11] 3,941,887
[45] Mar. 2, 1976

[54] DITHIOBIURET DERIVATIVES USED FOR REPELLING BIRDS, RODENTS, LEPORINE ANIMALS AND RUMINANTS

[75] Inventors: Günther Hermann, Leverkusen, Germany; Peter Hoffmann, Hollywood, Calif.; Friedrich-Karl Rosendahl, Leverkusen, Germany; Ivar Ugi, Santa Monica, Calif.

[73] Assignee: Bayer Aktiengesellschaft, Leverkusen, Germany

[22] Filed: Nov. 28, 1973

[21] Appl. No.: 419,854

Related U.S. Application Data

[63] Continuation of Ser. No. 825,447, May 16, 1969, abandoned.

[30] Foreign Application Priority Data
May 20, 1968  Germany............................ 1767535

[52] U.S. Cl................................. 424/322; 424/301
[51] Int. Cl.² ...................... A01N 9/12; A01N 9/20
[58] Field of Search..................................... 424/322

[56] References Cited
UNITED STATES PATENTS
2,410,862  11/1946  Bousquet et al................... 424/295

OTHER PUBLICATIONS
Ugi et al., Chem. Abst., p. 8033, Vol. 60, (1964).
Dixit, Chem. Abst. Vol. 55, 1961, p. 16526.

Primary Examiner—Albert T. Meyers
Assistant Examiner—Allen J. Robinson
Attorney, Agent, or Firm—Burgess, Dinklage & Sprung

[57] ABSTRACT

Compositions and methods for repelling warm-blooded creatures, such as birds, rodents leporine animals and ruminants using N-(alkyl, cycloalkyl, phenoxycarbonyloxyalkyl, phenyl, alkyl-phenyl and alkyl-chloro-phenyl)-dithiobiuret derivatives.

3 Claims, No Drawings

DITHIOBIURET DERIVATIVES USED FOR REPELLING BIRDS, RODENTS, LEPORINE ANIMALS AND RUMINANTS

This is a continuation of application Ser. No. 825,447, filed May 16, 1969, now abandoned.

The present invention relates to and has for its objects the provision for new active compositions of certain n -(alkyl, cycloalkyl, phenoxycarbonyloxyalkyl, phenyl, alkyl-phenyl and alkyl-chloro-phenyl)-dithiobiuret derivatives, some of which are known, and which possess bird-, rodent-, leporine animal- and ruminant-repellent properties, in the form of mixtures of such compounds with inert solid dispersible carrier vehicles and/or inert liquid dispersible carrier vehicles containing a surface-active agent, and new methods for using such compounds especially for repelling warm-blooded creatures such as birds, rodents, leporine animals and ruminants, with other and further objects becoming apparent from a study of the within specification and accompanying examples.

It is already known that tetramethylthiouram disulfide (A) can be used for repelling rodents and ruminants. This active compound has attained a considerable significance in commercial practice.

It is also known that anthraquinone (B) can be used for repelling birds. This active compound has likewise attained a considerable importance in commercial practice, but exhibits no repellent effect on rodents, leporine animals or ruminants.

In this regard, the known members of the class of dithiobiuret derivatives to which the present invention relates, are not yet known to have any pesticidal or pest- or warm-blooded creature- repellent properties (but see the disclosure and claims regarding similar properties for analogous dithiobiuret derivatives in U.S. Pat. No. 3,627,890, filed May 16, 1969 and issued Dec. 14, 1971 of the same inventorship herewith).

It has now been found, in accordance with the present invention, that certain dithiobiuret derivatives, some of which are known, of the formula

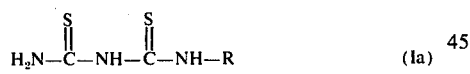

(Ia)

in which R is alkyl of 1–6 carbon atoms, cycloalkyl of 5–6 carbon atoms, phenoxycarbonyloxyalkyl having 1–4 carbon atoms in the corresponding alkyl moiety, phenyl, alkyl-substituted phenyl having 1–4 carbon atoms in each corresponding alkyl moiety, and alkyl-chlorophenyl having 1–4 carbon atoms in each corresponding alkyl moiety, exhibit a distinct repellent effect against birds, rodents, leporine animals and ruminants.

Surprisingly, the repellent effect of the active compounds of formula (Ia) above according to the present invention is higher than that of the known bird repellent anthraquinone (B) and the known rodent and ruminant repellent tetramethylthiouram disulfide (A). Therefore, the present invention represents a valuable contribution to the art.

The dithiobiuret derivatives of formula (Ia) above are already substantially known [cf. Liebigs Annalen der Chemie 670, 80 - 82 (1963)]. The still new dithiobiuret compounds of formula (Ia) above can be prepared suitably in the same manner as the known ones by addition of thiocyanic acid to the isonitriles and subsequent alkaline hydrolysis of the cyclic compounds which thereby form.

Advantageously, in accordance with the present invention, in the various formulae herein:

R represents alkyl hydrocarbon of 1–6 carbon atoms such as methyl, ethyl, n- and iso-propyl, n-, iso-, sec.- and tert.-butyl, n-amyl, 1-, 2- and 3-methyl-n-butyl, 1-ethyl-n-propyl, 1,1-and 1,2-dimethyl-n-propyl, n-hexyl, iso-hexyl, and the like, especially $C_{1-5}$, $C_{1-4}$, $C_{2-5}$, $C_{2-4}$, $C_{3-4}$, $C_{2-6}$, $C_{3-5}$, $C_{3-6}$ and $C_{4-6}$ alkyl, more especially $C_{1-4}$, $C_{2-5}$ and $C_{3-4}$ alkyl, and preferably iso-propyl and tert.-butyl;

cycloalkyl of 5–6 carbon atoms such as cyclopentyl, cyclohexyl, and the like, especially cyclohexyl;

phenoxycarbonyloxyalkyl having 1–4 carbon atoms in the corresponding alkyl moiety such as phenoxycarbonyloxy- methyl, eth-1 and 2-yl, prop-1,2 and 3-yl, but-1,2,3 and 4-yl, 2-methyl-propyl, 1,1-dimethylethyl, 2,2-dimethyl-ethyl and the like, i.e. phenoxycarbonyloxy-$C_{1-4}$ or $C_{2-4}$ alkyl, especially phenoxycarbonyloxy-1,1-dimethyl-ethyl;

phenyl;

alkyl-substituted phenyl having 1–4 carbon atoms in each corresponding alkyl moiety, i.e. which is substituted with 1 to 2 alkyl groups of 1–4 carbon atoms, such as methyl, ethyl, n- and iso-propyl, n-, iso-, sec.- and tert.-butyl substituted phenyl, especially mono and di (same and mixed) methyl to tert.-butyl inclusive as defined above, and the like, substituted phenyl, especially mono and di $C_{1-3}$ or $C_{1-2}$ alkyl substituted phenyl, more especially di $C_{1-4}$ or $C_{1-3}$ or $C_{1-2}$ alkyl-phenyl, most especially 2,6-di $C_{1-4}$ or $C_{1-3}$ or $C_{1-2}$ alkyl-phenyl, and preferably 2,6-di-methyl-phenyl; or alkyl-chloro-phenyl having 1–4 carbon atoms in the corresponding alkyl moiety such as methyl to tert.-butyl inclusive as defined above, and the like, -chloro-phenyl, i.e. 2-($C_{1-4}$ alkyl)-3,4,5 and 6-chloro-phenyl, or 2-chloro-3,4,5 and 6-($C_{1-4}$ alkyl)-phenyl, or 3-($C_{1-4}$ alkyl)-4 and 5-chloro-phenyl, or 3-chloro -4 and 5-($C_{1-4}$ alkyl)-phenyl, especially $C_{1-3}$ or $C_{1-2}$ alkyl-chloro-phenyl, more especially 2-($C_{1-4}$ or $C_{1-3}$ or $C_{1-2}$ alkyl) -3-chloro-phenyl, and most especially 2-methyl-3-chloro-phenyl.

Typical compounds of the present invention include:

N-1-isopropyl-dithiobiuret

N-1-tert.-butyl-dithiobiuret

N-1-cyclohexyl-dithiobiuret

N-1-[(1,1-dimethyl-2-phenoxycarbonyloxy)-ethyl]-dithiobiuret

N-1-(2'-methyl-3''-chlorophenyl)-dithiobiuret

N-1-(2',6'-dimethyl-phenyl)-dithiobiuret.

Advantageously, the active compounds according to the present invention possess, with low toxicity to warm-blooded animals, a pronounced repellant effect against destructive birds such as anserine birds (Anseriformes), gallinaceous birds (Galliformes), charadriiform birds (Charadriiformes), cuculine birds (Cuculiformes), passerine birds (Passeriformes); and the like.

The anserine birds contemplated herein include essentially the geese (Anseridae), such as ducks (Anatinae), and the like, whereas the gallinaceous birds contemplated herein include, in particular, the true fowls (Gallidae), such as ring-necked pheasant (*Phasianus colchicus*), and the like. Among the charadriiform birds contemplated herein, particularly important are the pigeons (Columbae); such as the wood pigeon (*Columba palumbus*) and the rock-dove (*Columba livia*)

with its domestic forms, and the like. In the case of the cuculine birds contemplated herein, the cuckoos (Cuculi), such as for example the plantain-eaters (Musophagidae), play a particular part, as do the parrots (Psittaci), for example the parakeets (Psittacinae), and the like. To the passerine birds contemplated herein there belong, in the main, the ravens (Corvidae), such as the carrion crow (*Corvus corone*) and the rock (*Corvus frugilegus*), the starlings (Sturnidae), the American blackbirds (Icteridae), the finches (Fringillidae), such as the sparrows (Passer spec.) and the weaver birds (Ploceidae), such as the red-billed weaver (*Quelea quelea*); and the like.

The compounds according to the present invention also exhibit a repellent effect against destructive leporine animals (Lagomorpha) and rodents (Rodentia), such as squirrel-like animals (Sciuroidae), gophers (Geomyoidae) and mouse-like animals (Muroidae) with which there are classed essentially the dormouse-like animals (Muscardinidae) and the mice (Muridae); and the like.

The leporine animals contemplated herein include essentially the Leporidae, such as the rabbit (*Oryctolagus cuniculus*), the squirrel-like animals include for example the European souslik (*Citellus citellus*), and the ground squirrel (*Citellus lateralis*), and the gophers include for example the mountain pocket gopher (*Thomomys talpoides*); and the like.

With the dormouse-like animals contemplated herein there is classed for example the fat dormouse (*Glis glis*), and the like, whereas the mice contemplated herein comprise essentially, in the group of the long-tailed mice (Murinae), the rats (Rattus spec.), such as the black rat (*Rattus rattus*) and the Norway rat (*Rattus norvegicus*); the house mice (Mus spec.), such as *Mus musculus*; in the group of the hamster-like animals (Cricetinae) the European hamster (*Cricetus cricetus*), and, in the group of the short-tailed mice (Microtinae) for example the common vole (*Microtus arvalis*), the field vole (*Microtus agrestis*) and the water vole (*Arvicola terrestris*); and the like.

The active compounds according to the present invention also repel destructive ruminants (Ruminantia), the most important groups of which are the deer (Cervidae) and the horned animals (Bovidae), and the like.

With the deer contemplated herein are classed for example the roe deer (*Capreolus capreolus*), the Virginia deer (Odocoileus spec.), the fallow deer (*Dama dama*), the wapiti (*Cervus canadensis*) and the red deer (*Cervus elaphus*), and the like. Among the horned animals contemplated herein, there belong to the group of the chamois-like animals (Rupicaprinae) particularly the sheep (ovis spec.) and goats (Capra spec.), and the like.

The active compounds according to the instant invention can be utilized, if desired, in the form of the usual formulations or compositions with conventional inert pesticidal (or pest- or warm-blooded creature-repellent) diluents or extenders, i.e. conventional pesticidal (or pest- or warm-blooded creature-repellent) dispersible carrier vehicles, such as solutions, emulsions, suspensions, emulsifiable concentrates, spray powders, pastes, soluble powders, dusting agents, granules, etc. These are prepared in known manner, for instance by extending the active compounds with conventional pesticidal (or pest- or warm-blooded creature-repellent) dispersible liquid diluent carriers and/or dispersible solid carriers optionally with the use of carrier vehicle assistants, e.g. conventional pesticidal (or pest- or warm-blooded creature- repellent) surface active agents, including emulsifying agents and/or dispersing agents, whereby, for example, in the case where water is used as diluent, organic solvents may be added as auxiliary solvents. The following may be chiefly considered for use as conventional carrier vehicles for this purpose: inert dispersible liquid diluent carriers, including inert organic solvents, such as aromatic hydrocarbons (e.g. benzene, toluene, xylene, etc.), halogenated, especially chlorinated, aromatic hydrocarbons (e.g. chlorobenzenes, etc.), paraffins (e.g. petroleum fractions), chlorinated aliphatic hydrocarbons (e.g. methylene chloride, etc.), alcohols (e.g. methanol, ethanol, propanol, butanol, etc.), amines (e.g. ethanolamine, etc.), ethers, ether-alcohols (e.g. glycol monomethyl ether, etc.), amides (e.g. dimethyl formamide, etc.), sulfoxides (e.g. dimethyl sulfoxide, etc.), ketones (e.g. acetone, etc.), and/or water; as well as inert dispersible finely divided solid carriers, such as ground natural minerals (e.g. kaolins, alumina, silica, chalk, i.e. calcium carbonate, talc, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other repellents, or nematocides, acaricides, insecticides, fungicides, herbicides, bactericides, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95%, and preferably 0.5–90%, by weight of the mixture, whereas carrier composition mixtures suitable for direct application or field application generally contemplate those in which the active compound is present in an amount substantially between about 0.01–95%, preferably 0.05–80%, more preferably 0.1–50%, and most preferably 0.5–30%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.01–95%, and preferably 0.01–80%, by weight of the mixture.

The active compounds can also be used in accordance with the well-known ultra-low-volume process with good success, i.e. by applying such compound if normally a liquid, or by applying a liquid composition containing the same, via very effective atomizing equipment in finely divided form, e.g. average particle diameter of from 50–100 microns, or even less, i.e. mist form, for example by airplane crop spraying techniques. Only up to at most about a few liters/ hectare are needed, and often amounts only up to about 1 quart/acre, preferably 2–16 fluid ounces/acre, are sufficient. In this process it is possible to use highly concentrated liquid compositions with said liquid carrier vehicles containing from about 20 to about 95% by weight of active compound or even the 100% active substance alone, e.g. about 20–100% by weight of the active compound.

In particular, the present invention contemplates methods of repelling warm-blooded creatures or animals, i.e. pests, and specifically birds, rodents, leporine animals and ruminants, which comprise applying to the area, material, place, and the like, from which such warm-blooded creatures are to be repelled, i.e. the locus to be protected or any and all things or matter which are susceptible to damage by (e.g. by eating, gnawing, biting, trampling, etc.) and/or from which such pest creatures are to be repelled, a correspondingly repellent effective amount, i.e. a warm-blooded creature repellent effective amount, of the particular active compound of the invention along or together with a carrier vehicle as noted above. The instant formulations or compositions are applied in the usual manner, for instance by spraying, atomizing, vaporizing, squirting, scattering, dusting, watering, sprinkling, pouring, and the like.

More specifically, application of the active compounds according to the present invention, their formulations and the application forms prepared therefrom is effected in the normal way, e.g. by seed treatment, by spraying, dusting or scattering of suitable preparations of the active compound on plants or parts of plants endangered or jeopardized by bird and/or rodent damage and/or damage by ruminants (including damage by game), by soil treatment, by fumigation in rooms or subterranean structures, by above-ground or underground application of repellent coatings and barriers and by impregnation of materials which may endangered or jeopardized by birds and/or rodents and/or ruminants, such as wood, paper, rubber and synthetic materials.

For seed treatment, e.g. seed dressing, in general substantially between about 0.01–5, preferably between about 0.025–1, parts by weight of active compound are used per 100 parts by weight of seed, e.g. per 100 g of seed, i.e. plantable or agricultural crop seed.

Spray liquors or pastes usable for the achievement of bird-repellent, rodent-repellent and ruminant-repellent coatings, e.g. on endangered or jeopardized plants or parts of plants, contain, in general, substantially between about 0.1–20, preferably between about 0.5–10, per cent by weight of active compound. Materials which are soaked or impregnated with the active compounds should have in the surface layer thereof a concentration of active compound of substantially between about 0.1–5 per cent by weight.

It will be realized, of course, that the concentration of the particular active compound utilized in admixture with the carrier vehicle may vary within a fairly wide range and will depend upon the intended application as the artisan will appreciate. Therefore, in special cases it is possible to go above or below the aforementioned concentration ranges.

The outstanding effectiveness of the particular compounds usable according to the present invention is illustrated, without limitation, by the following Examples.

EXAMPLE 1

A. Repellent test/domestic pigeon

Test creature: domestic pigeon (*Columba livia*)

To prepare a suitable mixture of the particular active compound, 3 parts by weight of such active compound are mixed with 2.8 parts by weight of highly dispersed silicic acid and 4.3 parts by weight of talc. 6 parts by weight of the resulting active compound concentrate are intimately mixed with 1000 parts by weight of wheat seed and the mixture after addition of 11 parts by weight of polyethylene glycol as adhesive, is shaken until the seed is uniformly impregnated. The content of active compound is thus 0.18%.

120 g of the wheat so impregnated are placed in a plastic container provided with a circular aperture in the front wall. This container is placed in front of two feral pigeons kept together. No untreated food is available to the animals; they receive as much water as they wish. The experiment proceeds for 60 hours under continuous light.

The residual amount of treated seed, i.e. which has not been eaten, is weighed again after the experiment. This figure, expressed as a percentage of the amount originally used, is valid as a measure of the repellent effect. Thus, 100% means that no wheat is eaten, the repellent effect being consequently total.

The particular active compounds tested, the repellent effect and the number of individual experiments can be seen from the first three columns of the following Table 1:

B. Repellent test/house mouse

Test creature: white Laboratory mouse (*Mus musculus*)

Concentration of active compound in test food: 0.5%

To produce a suitable preparation of the particular active compound, 3 parts by weight of such active compound are mixed with 2.8 parts by weight of highly dispersed silicic acid and 4.2 parts by weight of talc. To prepare the test bait, 1.67 parts by weight of the resulting active compound concentrate are intimately mixed with 95 parts by weight of a standard mealy food customary for feeding experimental animals, with the addition of 3.33 parts by weight of methyl cellulose and a little water. From 6 g of the resulting dry substance, two spherical bait pellets are formed which are dried at room temperature for 24 hours before commencement of the experiment.

The pellets are placed for 24 hours, without other food, before two white laboratory mice kept together. Water is freely available. The residues of the pellets are dried and weighed again after the experiment has ended.

The residual amount, expressed as a percentage of the amount originally used, is valid as a measure of the repellent effect. Thus, 100% repellent effect means that nothing at all of the pellets has been eaten.

The particular active compounds tested, the number of experiments and the results obtained can be seen from the first, fourth and fifth columns of the following Table 1:

containing active compound and planted in an open-air game enclosure of 1.01 hectares. Inside the enclosed open-air area, 10 test plots are laid out in each of which there are 20 seedlings which are treated with the given Table 1

| Active compound | | Repellent test/domestic pigeon | | Repellent test/house mouse | |
|---|---|---|---|---|---|
| | | Number of individual experiments | Repellent effect in % (average value) | Number of individual experiments | Repellent effect in % (average value) |
| (A) | Tetramethylthiouram disulfide (known) | 3 | 49.7 | 2 | 60.0 |
| (B) | Anthraquinone (known) | 2 | 47.4 | 3 | 0 |
| ($1a_1$) | $H_2N-CS-NH-CS-NH-CH(CH_3)_2$ | — | — | 3 | 82.8 |
| ($2a_1$) | $H_2N-CS-NH-CS-NH-C(CH_3)_3$ | — | — | 2 | 81.7 |
| ($3a_1$) | $H_2N-CS-NH-CS-NH-\text{(phenyl)}$ | 1 | 69.1 | — | — |
| ($4a_1$) | $H_2N-CS-NH-CS-NH-C(CH_3)_2-CH_2-O-CO-O-\text{(phenyl)}$ | — | — | 3 | 90.0 |
| ($5a_1$) | $H_2N-CS-NH-CS-NH-\text{(3,5-dimethylphenyl)}$ | 1 | 82.5 | 3 | 83.9 |
| ($6a_1$) | $H_2N-CS-NH-CS-NH-\text{(3-methyl-4-chlorophenyl)}$ | 3 | 89.1 | 4 | 83.3 |

EXAMPLE 2

Open-air enclosure test/black-tailed deer

Test creature: Black-tailed deer (*Odocoileus columbianus*)

To produce a suitable preparation of the particular active compound, 6 parts by weight of such active compound and 10 parts by weight of a copolymer of methacrylic acid methyl ester and butadiene as adhesion promoter are dispersed in 84 parts by weight of water. Two-year-old Douglas fir seedlings (*Pseudotsuga taxifolia*) 18–30 cm high are totally immersed in the active compound preparation. After drying, the plants are covered all over with a thin film of the adhesive containing active compound and planted in an open-air game enclosure of 1.01 hectares. Inside the enclosed open-air area, 10 test plots are laid out in each of which there are 20 seedlings which are treated with the given active compound, 20 seedlings which are treated with the standard agent tetramethylthiouram disulfide (TMTD) and 20 seedlings which are untreated and which serve as control.

The game enclosure is then occupied by 10 black-tailed deer. The test proceeds until intermediate checks show a damage of 60–80% in the case of the untreated seedlings. Then the average degree of damage is determined. 100 means that all the seedlings have been damaged, whereas 0 means that none of the seedlings have been damaged.

The particular active compounds tested, dosages, number of treated seedlings and average degrees of damage can be seen from the following Table 2.

Table 2

| Active compound | | Enclosed open-air area test/black-tailed deer | | |
|---|---|---|---|---|
| | | Dosage of active compound in the treatment medium in % | Number of treated seedlings | Average degree of damage |
| (A) | Tetramethylthiouram disulfide (known) | 6 | 200 | 47.91 |
| | untreated control | — | 200 | 74.87 |
| ($6a_2$) | $H_2N-CS-NH-CS-NH-\text{(3-methyl-4-chlorophenyl)}$ | 6 | 200 | 26.45 |

It will be realized that all the foregoing compounds contemplated by the present invention possess the desired warm-blooded creature or animal repellent properties for repelling birds, rodents, leporine animals and ruminants, and that such compounds have not only a very slight toxicity toward warm-blooded creatures, but also a concomitantly low phytotoxicity.

It will be appreciated that the instant specification and examples are set forth by way of illustration and not limitation, and that various modifications and changes may be made without departing from the spirit and scope of the present invention.

What is claimed is:

1. A method for repelling warm-blooded creatures selected from the group consisting of birds, rodents, leporine animals and ruminants, which comprises fumigating structures from which it is desired to exclude said warm-blooded creatures with an effective amount for repelling such creatures of a dithiobiuret compound of the formula

in which R is selected from the group consisting of alkyl of 1–6 carbon atoms, cycloalkyl of 5–6 carbon atoms, phenyl, alkyl-substituted phenyl having 1–4 carbon atoms in each corresponding alkyl moiety, and alkyl-chloro-phenyl having 1–4 carbon atoms in the alkyl moiety.

2. The method of claim 1 wherein said compound is N-1-(2′, 6′-dimethyl-phenyl)-dithiobiuret of the formula

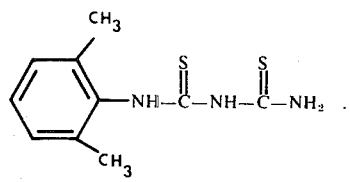

3. A method for repelling house mice which comprises applying to a locus from which said house mice are to be repelled, an effective amount for repelling such house mice of N-1-(2′, 6′-dimethyl-phenyl)-dithiobiuret of the formula

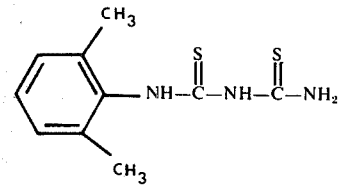

* * * * *